(12) United States Patent
Solomon

(10) Patent No.: US 10,213,349 B2
(45) Date of Patent: Feb. 26, 2019

(54) PATIENT INCONTINENCE AND LIFTING PAD

(71) Applicant: Charleen Suzanne Solomon, Oakdale, CA (US)

(72) Inventor: Charleen Suzanne Solomon, Oakdale, CA (US)

(*) Notice: Subject to any disclaimer, the term of this patent is extended or adjusted under 35 U.S.C. 154(b) by 263 days.

(21) Appl. No.: 15/053,100

(22) Filed: Feb. 25, 2016

(65) Prior Publication Data

US 2016/0242966 A1 Aug. 25, 2016

Related U.S. Application Data

(60) Provisional application No. 62/120,512, filed on Feb. 25, 2015.

(51) Int. Cl.
*A61F 13/15* (2006.01)
*A61F 13/64* (2006.01)
*A61F 13/62* (2006.01)
*A61F 13/56* (2006.01)

(52) U.S. Cl.
CPC ............ *A61F 13/64* (2013.01); *A61F 13/622* (2013.01); *A61F 2013/15146* (2013.01); *A61F 2013/5661* (2013.01)

(58) Field of Classification Search
CPC .............. A61F 13/64; A61F 13/622; A61F 2013/15146; A61F 2013/5661; A61F 2013/15154
USPC ................. 604/391, 385.11, 385.14, 385.28
See application file for complete search history.

(56) References Cited

U.S. PATENT DOCUMENTS

| | | | | |
|---|---|---|---|---|
| 4,675,925 A * | 6/1987 | Littleton | ............. | A61G 7/1026 5/484 |
| 5,787,523 A * | 8/1998 | Lindberg | ............. | A47G 9/0238 5/484 |
| 6,154,900 A * | 12/2000 | Shaw | ..................... | A61G 7/001 5/615 |
| 7,818,836 B2 * | 10/2010 | Stinson | .................. | A61G 7/001 5/487 |
| 8,161,583 B1 * | 4/2012 | Palen | ..................... | A61G 7/001 5/81.1 HS |
| 9,480,613 B1 * | 11/2016 | Lackey | ................ | A61G 7/1023 |
| 2005/0055768 A1 * | 3/2005 | Assink | ..................... | A61G 1/01 5/81.1 R |
| 2007/0056096 A1 * | 3/2007 | Assink | ................... | A47C 27/14 5/81.1 HS |
| 2011/0296609 A1 * | 12/2011 | Giap | ..................... | A61G 7/1023 5/88.1 |
| 2014/0352072 A1 * | 12/2014 | Holladay | ............. | A61G 13/126 5/655.5 |

* cited by examiner

*Primary Examiner* — Jacqueline Stephens

(57) ABSTRACT

A patient incontinence and lifting pad is an apparatus utilized to absorb urine excreted by a bedridden patient as well as to facilitate turning and lifting the patient. The apparatus includes a bed pad on which the patient is able to lie as well as an attached first securing strap and a second securing strap used to anchor the bed pad to a hospital bed railing or similar structure. An elongated band of the first securing strap and the second securing strap may be attached to itself in order to anchor the bed pad. An absorbent incontinence pad insert for absorbing urine is inserted within a slot on the bed pad and may be removable/replaceable. The absorbent incontinence pad insert may be held in place within the slot by a peripheral hook fastener strip.

14 Claims, 6 Drawing Sheets

PATIENT INCONTINENCE AND LIFTING PAD

The current application claims a priority to the U.S. Provisional Patent application Ser. No. 62/120,512 filed on Feb. 25, 2015.

FIELD OF THE INVENTION

The present invention relates generally to a pad for use in hospital or home beds. More specifically, the present invention is a patient incontinence and lifting pad that facilitates turning and moving a bedridden patient.

BACKGROUND OF THE INVENTION

A common hazard of the health industry is the possibility of back injury when handling patients who are unable to move of their own accord. Work-related injuries such as musculoskeletal disorders may result from performing high-risk tasks and can affect all aspects of life. These injuries result in exorbitant medical costs and workers' compensation costs. Within the health industry, one of the largest causes of injuries is unsafe lifting practices, particularly when handling bedridden patients. This can be problematic as bedridden patients who are unable to move on their own must be turned frequently in order to prevent the onset of pressure ulcers. Simply turning bedridden patients can be a challenging task in itself. Moving bedridden patients altogether can be even more difficult and may result in injury to health personnel with unsafe lifting practices.

The present invention is a patient incontinence and lifting pad. The present invention is utilized to absorb urine that is excreted by bedridden patients as well as to aid health personnel in turning and moving bedridden patients. The present invention greatly mitigates the likelihood of back injuries and similar ailments due to unsafe lifting practices. When using the present invention, health personnel are not required to directly physically handle bedridden patients during turning and moving. The present invention may be reusable.

DETAIL DESCRIPTIONS OF THE INVENTION

Figure 1:
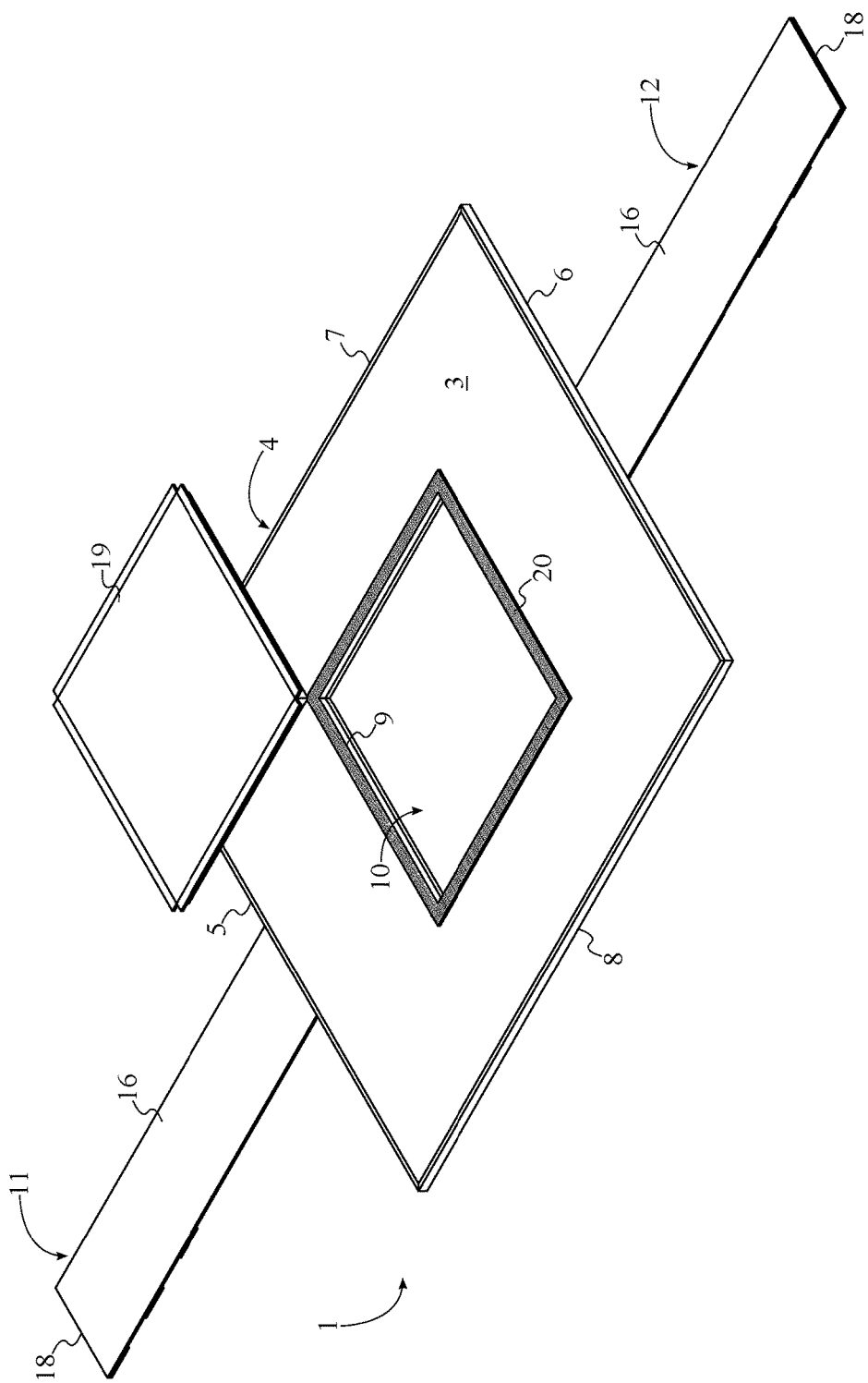
FIG. 1 is a top exploded perspective view of the present invention.
Figure 2:
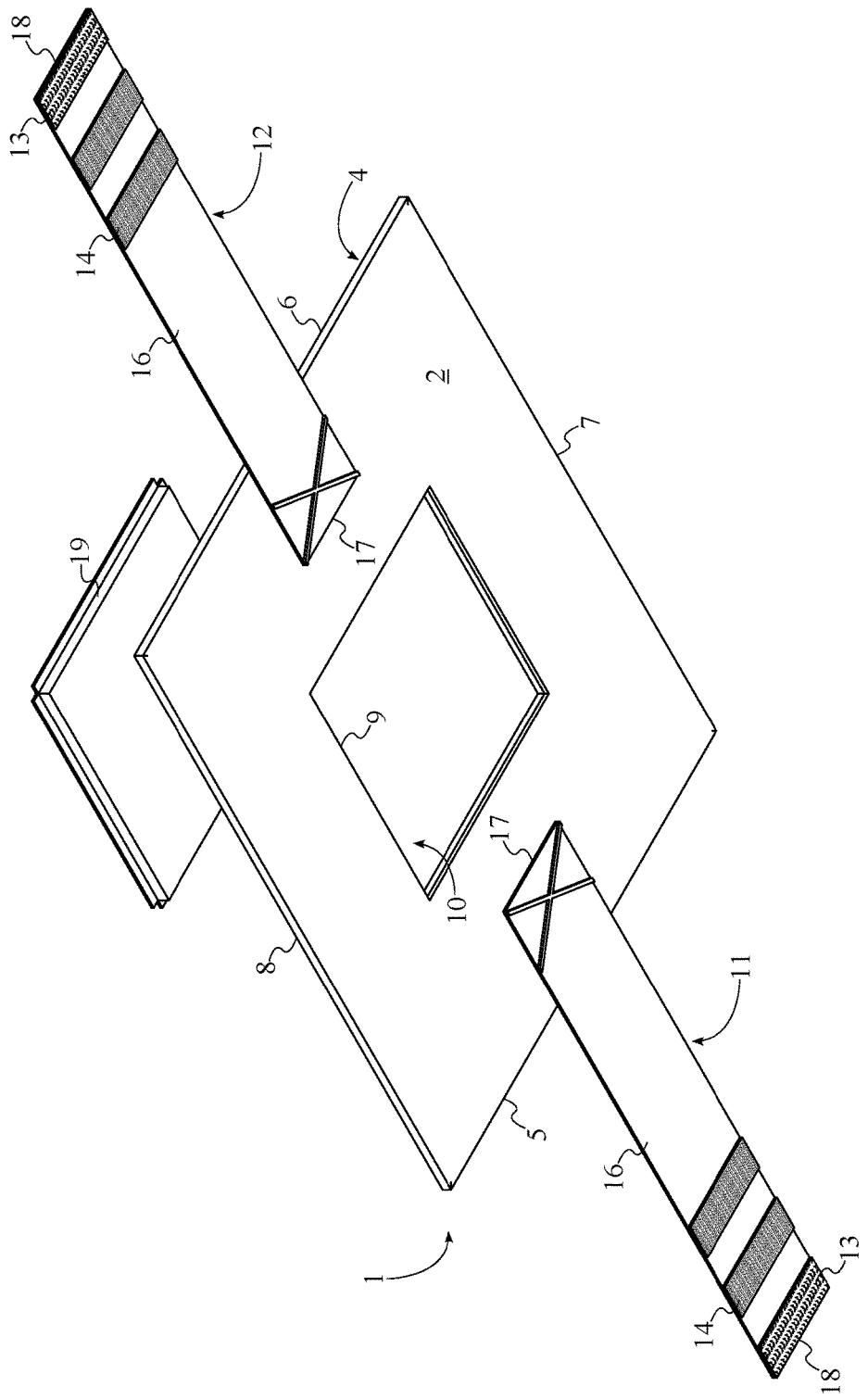
FIG. 2 is a bottom exploded perspective view of the present invention.
Figure 3:
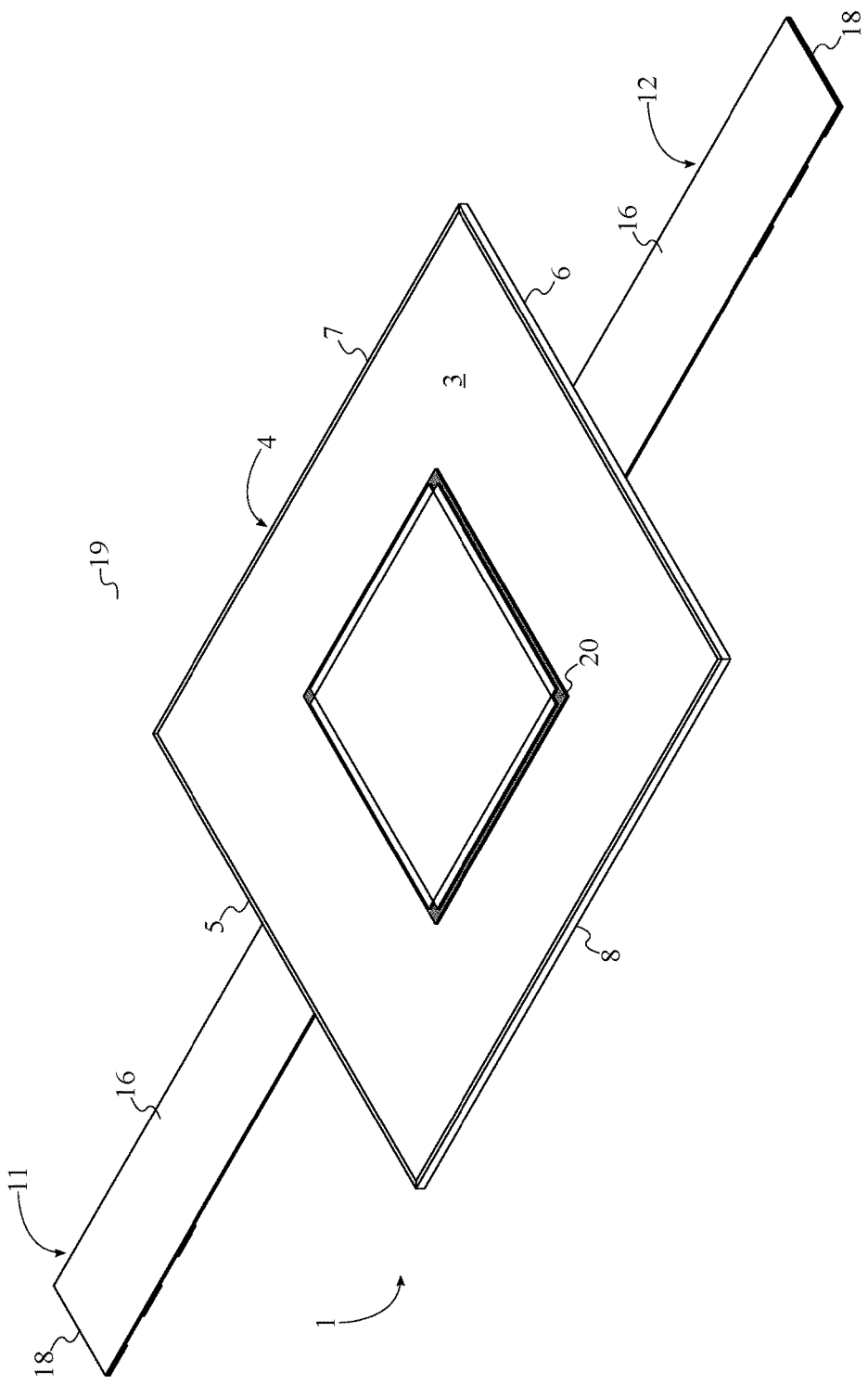
FIG. 3 is a top perspective view of the present invention.
Figure 4:
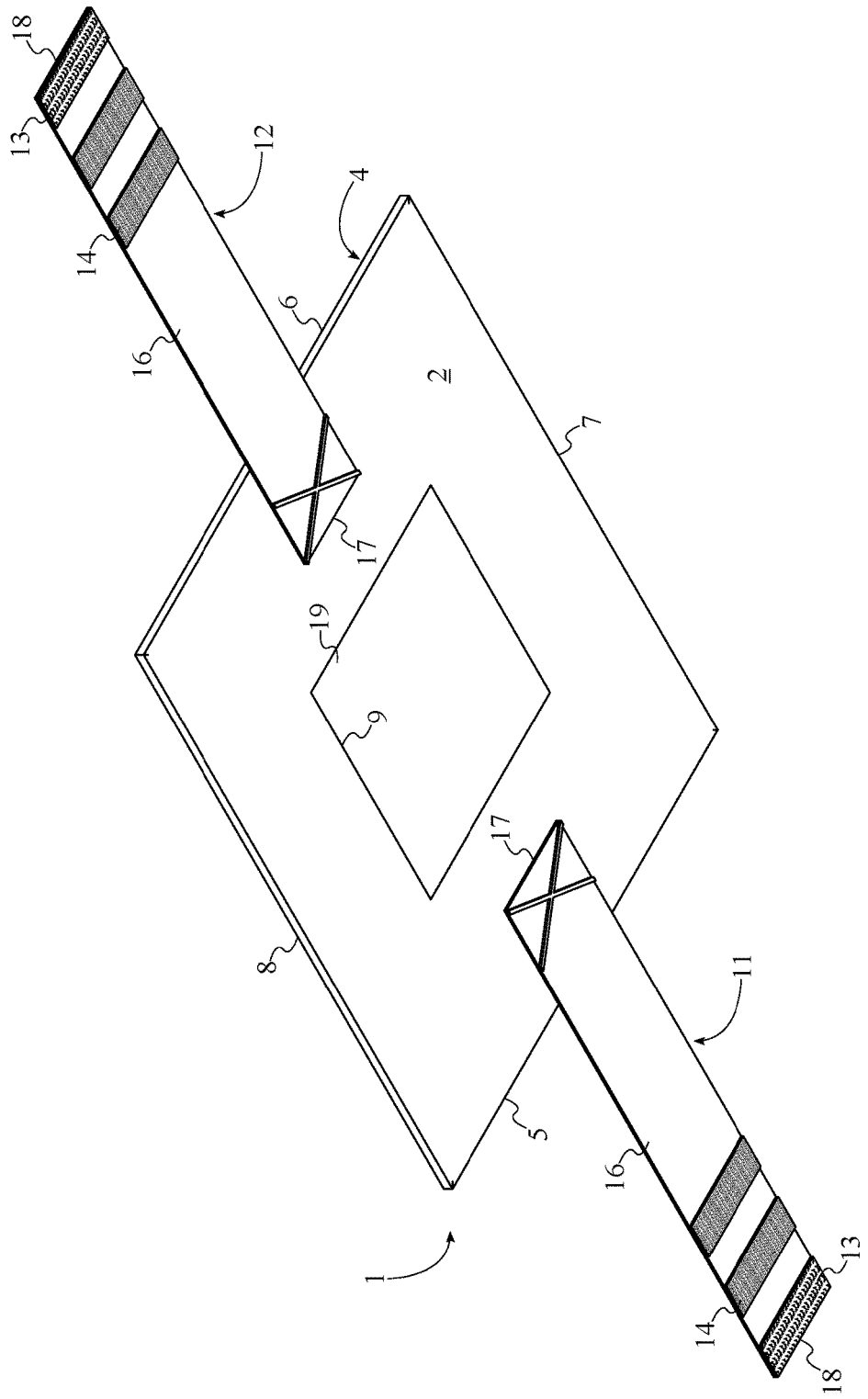
FIG. 4 is a bottom perspective view of the present invention.

All illustrations of the drawings are for the purpose of describing selected versions of the present invention and are not intended to limit the scope of the present invention.

The present invention is a patient incontinence and lifting pad that facilitates turning and moving a bedridden patient. The present invention is shown in FIGS. 1-4 and comprises a bed pad 1, a first securing strap 11, a second securing strap 12, and an absorbent incontinence pad insert 19.

The bed pad 1 is a pad that may be placed onto a hospital bed or similar surface. The bed pad 1 comprises a base surface 2, a cover surface 3, an outer edge 4, an inner edge 9, and a slot 10. The base surface 2 and the cover surface 3 are opposite surfaces of the bed pad 1. The base surface 2 is the surface of the base pad that is placed into contact with the hospital bed during use of the invention while the cover surface 3 is the surface of the bed pad 1 on which a patient is able to lie.

The first securing strap 11 and the second securing strap 12 are utilized to fasten the bed pad 1 to a hospital bed railing or similar structure in order to ensure that the bed pad 1 is not subjected to unwanted movement during use. The first securing strap 11 and the second securing strap 12 additionally are utilized to anchor the bed pad 1 when turning or moving a patient. The first securing strap 11, the second securing strap 12, or both may be utilized to anchor one side or both sides of the bed pad 1. Anchoring one side of the bed pad 1 enables the patient to be turned. For example, if the first securing strap 11 or the second securing strap 12 is secured to a hospital bed railing, the hospital bed may then be lowered while the hospital bed railing remains stationary. As the hospital bed is lowered, the anchored side of the bed pad 1 becomes elevated, simultaneously lifting the corresponding side of the patient and greatly facilitating turning the patient onto his or her front or back side as the patient does not need to be manually turned. Both the first securing strap 11 and the second securing strap 12 are secured to a hospital bed railing in order to facilitate moving the patient. If both the first securing strap 11 and the second securing strap 12 are secured to the hospital bed railing, the entire bed pad 1 becomes elevated along with the patient. The patient may then be easily moved without being required to be manually lifted.

The first securing strap 11 is connected onto the base surface 2, adjacent to the outer edge 4. Similarly, the second securing strap 12 is connected onto the base surface 2, opposite to the first securing strap 11. The first securing strap 11 and the second securing strap 12 are thus kept out of the way and positioned in a manner such that a patient lying on the cover surface 3 does not interfere with the functionality of the first securing strap 11 and the second securing strap 12. Because the first securing strap 11 and the second securing strap 12 are positioned adjacent to the outer edge 4, the bed pad 1 may be elevated when the hospital bed is lowered.

The slot 10 is delineated by the inner edge 9 and is sufficiently sized to accommodate the absorbent incontinence pad insert 19 within the slot 10. When the present invention is utilized with an incontinent patient, the absorbent incontinence pad insert 19 is able to absorb excreted urine. The slot 10 traverses through the bed pad 1 from the cover surface 3 to the base surface 2, thus traversing completely through the bed pad 1. The absorbent incontinence pad insert 19 is positioned within the slot 10, allowing the absorbent incontinence pad insert 19 to be held in place within the slot 10 during use of the present invention. The absorbent incontinence pad insert 19 is peripherally mounted to the cover surface 3, positioning the absorbent incontinence pad insert 19 next to the patient and preventing the absorbent incontinence pad insert 19 from separating from the bed pad 1 during use of the present invention. In the preferred embodiment of the present invention, the slot 10 is positioned centrally on the bed pad 1, positioning the absorbent incontinence pad insert 19 to most effectively absorb excreted urine. The absorbent incontinence pad insert 19 may be removably mounted to the cover surface 3. This allows the present invention to be reusable as the absorbent incontinence pad insert 19 may simply be replaced after being sullied. The bed pad 1 may be washable and reusable as well.

Because the present invention is intended for use with incontinent patients, in the preferred embodiment of the present invention, the bed pad 1, the first securing strap 11, the second securing strap 12, and the absorbent incontinence pad insert 19 are composed of superabsorbent polymer. Superabsorbent polymer is able to absorb and retain large amounts of liquid relative to its own mass and, as such, is suitable for use in the present invention.

The present invention further comprises a peripheral hook fastener strip 20. The peripheral hook fastener strip 20 is utilized to secure the absorbent incontinence pad insert 19 to the bed pad 1 in reusable embodiments of the present invention. The peripheral hook fastener strip 20 is connected around the inner edge 9 on the cover surface 3. This allows the peripheral hook fastener strip 20 to hold the absorbent incontinence pad insert 19 to the inner edge 9. The absorbent incontinence pad insert 19 is removably engaged to the peripheral hook fastener strip 20. When the absorbent incontinence pad insert 19 has been used, the absorbent incontinence pad insert 19 may simply be separated from the peripheral hook fastener strip 20 and replaced.

The outer edge 4 comprises a left edge 5 and a right edge 6 that are opposing edges of the outer edge 4. The first securing strap 11 is connected onto the base surface 2, adjacent to the left edge 5. Similarly, the second securing strap 12 is connected onto the base surface 2, adjacent to the right edge 6. The first securing strap 11 and the second securing strap 12 are thus positioned opposite to each other on the base surface 2, enabling the left edge 5 and the right edge 6 to be lifted as needed when the present invention is in use. The first securing strap 11 is oriented perpendicular to the left edge 5 while the second securing strap 12 is oriented perpendicular to the right edge 6. The first securing strap 11 and the second securing strap 12 are thus aligned with each other, ensuring stability of the bed pad 1 when the bed pad 1 is lifted.

The outer edge 4 additionally comprises a top edge 7 and a bottom edge 8 that are opposing edges of the outer edge 4. The first securing strap 11 and the second securing strap 12 are centrally positioned in between the top edge 7 and the bottom edge 8. The first securing strap 11 and the second securing strap 12 are thus positioned equally distant from the top edge 7 and the bottom edge 8 for stability of the bed pad 1 during lifting.

Figure 5:
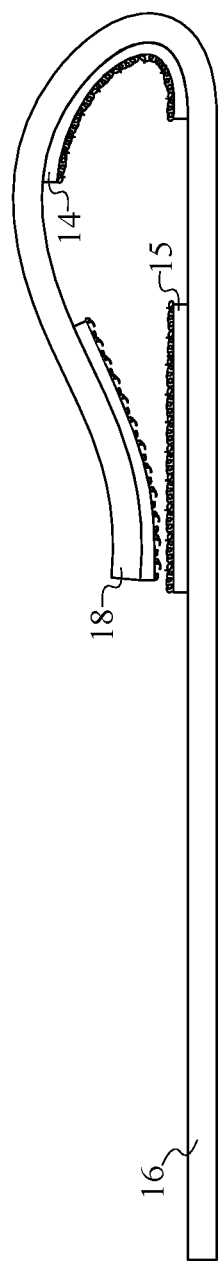
FIG. 5 is a side view of the elongated band being secured to itself.

The first securing strap 11 and the second securing strap 12 each comprise a hook fastener strip 13, at least one loop fastener strip 14, and an elongated band 16. The hook fastener strip 13 and the at least one loop fastener strip 14 enable the elongated band 16 to be secured to itself when anchoring the bed pad 1 through the first securing strap 11 and the second securing strap 12. The elongated band 16 comprises a fixed end 17 and a free end 18 that are opposite ends of the elongated band 16. The free end 18 may be handled by the user when utilizing the first securing strap 11 and the second securing strap 12. The fixed end 17 is fixed onto the base surface 2, ensuring that the first securing strap 11 and the second securing strap 12 remain secured to the base surface 2 during use of the present invention. The hook fastener strip 13 is positioned adjacent to the free end 18, enabling the hook fastener strip 13 to be utilized to secure the elongated band 16 to itself by fastening the free end 18 to the at least one loop fastener strip 14. The at least one loop fastener strip 14 is offset from the hook fastener strip 13 on the elongated band 16, allowing the elongated band 16 to be folded and secured to itself. The at least one loop fastener strip 14 preferably includes two or more loop fastener strips to enable adjustability for the first securing strap 11 and the second securing strap 12. The hook fastener strip 13 and the at least one loop fastener strip 14 are oriented away from the base surface 2. Because the hook fastener strip 13 and the at least one loop fastener strip 14 are positioned on the same surface of the elongated band 16, the hook fastener strip 13 may be secured to the at least one loop fastener strip 14 when the elongated band 16 is attached to itself. As shown in FIG. 5, the hook fastener strip 13 is removably engaged to a selected strip 15 from the at least one loop fastener strip 14. The hook fastener strip 13 may thus be easily fastened to and unfastened from the selected strip 15.

Figure 6:
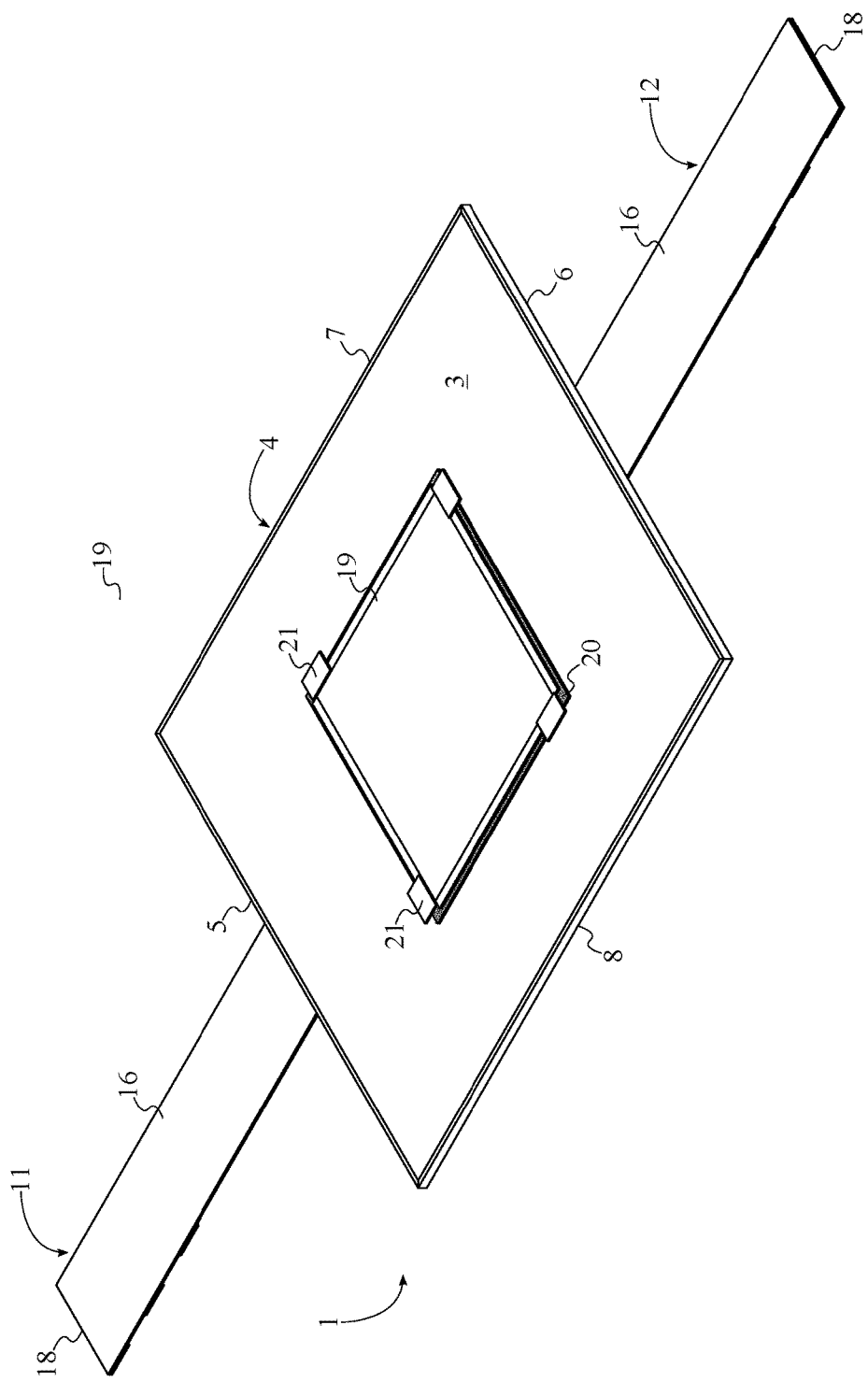
FIG. 6 is a perspective view of an embodiment of the present invention with pull tabs.

As shown in FIG. 6, the present invention may further comprise a plurality of pull tabs 21. The plurality of pull tabs 21 facilitates the separation of the absorbent incontinence pad insert 19 from the bed pad 1 when the absorbent incontinence pad insert 19 requires replacement. The plurality of pull tabs 21 is perimetrically distributed about the absorbent incontinence pad insert 19, allowing removal of the absorbent incontinence pad insert 19 from multiple sides.

Although the present invention has been explained in relation to its preferred embodiment, it is understood that many other possible modifications and variations can be made without departing from the spirit and scope of the present invention as hereinafter claimed.

What is claimed is:

1. A patient incontinence and lifting pad comprises:
 a bed pad;
 a first securing strap;
 a second securing strap;
 an absorbent incontinence pad insert;
 the bed pad comprises a base surface, a cover surface, an outer edge, an inner edge, and a slot;
 the base surface and the cover surface being opposite surfaces of the bed pad;
 the first securing strap being connected onto the base surface, adjacent to the outer edge;
 the second securing strap being connected onto the base surface, opposite to the first securing strap;
 the slot traversing through the bed pad from the cover surface to the base surface;
 the slot being delineated by the inner edge;
 the absorbent incontinence pad insert being positioned within the slot;
 the absorbent incontinence pad insert being peripherally mounted to the cover surface; and
 the bed pad, the first securing strap, the second securing strap, and the absorbent incontinence pad insert are composed of superabsorbent polymer.

2. The patient incontinence and lifting pad as claimed in claim 1 further comprises:
 the slot being positioned centrally on the bed pad.

3. The patient incontinence and lifting pad as claimed in claim 1 further comprises:
 the absorbent incontinence pad insert being removably mounted to the cover surface.

4. The patient incontinence and lifting pad as claimed in claim 3 further comprises:
 a peripheral hook fastener strip;
 the peripheral hook fastener strip being connected around the inner edge on the cover surface; and
 the absorbent incontinence pad insert being removably engaged to the peripheral hook fastener strip.

5. The patient incontinence and lifting pad as claimed in claim 1 further comprises:
the outer edge comprises a left edge and a right edge;
the first securing strap being connected onto the base surface, adjacent to the left edge;
the second securing strap being connected onto the base surface, adjacent to the right edge;
the first securing strap being oriented perpendicular to the left edge; and
the second securing strap being oriented perpendicular to the right edge.

6. The patient incontinence and lifting pad as claimed in claim 1 further comprises:
the outer edge comprises a top edge and a bottom edge; and
the first securing strap and the second securing strap being centrally positioned in between the top edge and the bottom edge.

7. The patient incontinence and lifting pad as claimed in claim 1 further comprises:
the first securing strap and the second securing strap each comprise a hook fastener strip, at least one loop fastener strip, and an elongated band;
the elongated band comprises a fixed end and a free end;
the fixed end and the free end being opposite ends of the elongated band;
the fixed end being fixed onto the base surface;
the hook fastener strip being positioned adjacent to the free end;
the at least one loop fastener strip being offset from the hook fastener strip on the elongated band;
the hook fastener strip and the at least one loop fastener strip being oriented toward the base surface; and
the hook fastener strip being removably engaged to a selected strip from the at least one loop fastener strip.

8. The patient incontinence and lifting pad as claimed in claim 1 further comprises:
a plurality of pull tabs; and
the plurality of pull tabs being perimetrically distributed about the absorbent incontinence pad insert.

9. A patient incontinence and lifting pad comprises:
a bed pad;
a first securing strap;
a second securing strap;
an absorbent incontinence pad insert;
a peripheral hook fastener strip;
the bed pad comprises a base surface, a cover surface, an outer edge, an inner edge, and a slot;
the base surface and the cover surface being opposite surfaces of the bed pad;
the first securing strap being connected onto the base surface, adjacent to the outer edge;
the second securing strap being connected onto the base surface, opposite to the first securing strap;
the slot traversing through the bed pad from the cover surface to the base surface;
the slot being delineated by the inner edge;
the absorbent incontinence pad insert being positioned within the slot;
the absorbent incontinence pad insert being peripherally mounted to the cover surface;
the absorbent incontinence pad insert being removably mounted to the cover surface;
the peripheral hook fastener strip being connected around the inner edge on the cover surface;
the absorbent incontinence pad insert being removably engaged to the peripheral hook fastener strip; and
the bed pad, the first securing strap, the second securing strap, and the absorbent incontinence pad insert are composed of superabsorbent polymer.

10. The patient incontinence and lifting pad as claimed in claim 9 further comprises:
the slot being positioned centrally on the bed pad.

11. The patient incontinence and lifting pad as claimed in claim 9 further comprises:
the outer edge comprises a left edge and a right edge;
the first securing strap being connected onto the base surface, adjacent to the left edge;
the second securing strap being connected onto the base surface, adjacent to the right edge;
the first securing strap being oriented perpendicular to the left edge; and
the second securing strap being oriented perpendicular to the right edge.

12. The patient incontinence and lifting pad as claimed in claim 9 further comprises:
the outer edge comprises a top edge and a bottom edge; and
the first securing strap and the second securing strap being centrally positioned in between the top edge and the bottom edge.

13. The patient incontinence and lifting pad as claimed in claim 9 further comprises:
the first securing strap and the second securing strap each comprise a hook fastener strip, at least one loop fastener strip, and an elongated band;
the elongated band comprises a fixed end and a free end;
the fixed end and the free end being opposite ends of the elongated band;
the fixed end being fixed onto the base surface;
the hook fastener strip being positioned adjacent to the free end;
the at least one loop fastener strip being offset from the hook fastener strip on the elongated band;
the hook fastener strip and the at least one loop fastener strip being oriented toward the base surface; and
the hook fastener strip being removably engaged to a selected strip from the at least one loop fastener strip.

14. The patient incontinence and lifting pad as claimed in claim 9 further comprises:
a plurality of pull tabs; and
the plurality of pull tabs being perimetrically distributed about the absorbent incontinence pad insert.

* * * * *